United States Patent [19]

Shene

[11] Patent Number: 5,627,324

[45] Date of Patent: May 6, 1997

[54] PEAK FLOW METER

[75] Inventor: William R. Shene, Plattsburgh, N.Y.

[73] Assignee: Trudell Medical Limited, Canada

[21] Appl. No.: 344,530

[22] Filed: Nov. 23, 1994

Related U.S. Application Data

[63] Continuation of Ser. No. 153,091, Nov. 17, 1993, abandoned.

[51] Int. Cl.$^6$ .................................................. A16B 5/08
[52] U.S. Cl. ............................... 73/861.53; 128/725
[58] Field of Search ..................... 73/861.53–861.56, 73/861.58, 861.71, 861.74; 128/725, 727; 116/273, 272, 264

[56] References Cited

U.S. PATENT DOCUMENTS

| | | |
|---|---|---|
| D. 263,166 | 2/1982 | Bushman . |
| 471,389 | 3/1892 | Lacey . |
| 599,746 | 3/1898 | St. John ............................ 73/861.58 |
| 1,541,750 | 6/1925 | Park . |
| 2,061,852 | 11/1936 | Schweitzer ........................ 73/861.58 |
| 3,298,362 | 1/1967 | Lippitt, Jr. et al. . |
| 3,635,214 | 1/1972 | Rand et al. . |
| 3,720,202 | 3/1973 | Cleary . |
| 3,826,247 | 7/1974 | Ruskin et al. . |
| 3,862,628 | 1/1975 | Williams ........................... 73/861.74 |
| 3,940,984 | 3/1976 | Oram . |
| 3,958,565 | 5/1976 | Wright . |
| 4,019,382 | 4/1977 | El-Gammal . |
| 4,041,935 | 8/1977 | Garbe ............................... 128/727 |
| 4,227,409 | 10/1980 | Bingler ............................. 73/861.71 |
| 4,259,967 | 4/1981 | Vooren et al. . |
| 4,287,775 | 9/1981 | Hutton . |
| 4,292,853 | 10/1981 | Williams et al. . |
| 4,294,262 | 10/1981 | Williams et al. . |
| 4,421,120 | 12/1983 | Edwards, Jr. et al. . |
| 4,533,137 | 8/1985 | Sonne . |
| 4,640,293 | 2/1987 | Garbe et al. . |
| 4,768,520 | 9/1988 | Varraux et al. ................... 128/725 |
| 4,944,306 | 7/1990 | Alvino . |
| 4,967,596 | 11/1990 | Rilling et al. . |
| 5,246,010 | 9/1993 | Gazzara et al. .................. 128/725 |
| 5,320,107 | 6/1994 | O'Brien ............................ 128/725 |

FOREIGN PATENT DOCUMENTS

| | | |
|---|---|---|
| WO91/11140 | 8/1991 | European Pat. Off. . |
| 267933 | 6/1927 | United Kingdom . |
| 1160669 | 8/1969 | United Kingdom . |
| WO93/06778 | 4/1993 | WIPO . |

OTHER PUBLICATIONS

Advertisement for "Assess Peak Flow Meter", believed to be published prior to Nov. 17, 1993.
Advertisement for "Personal Best Peak Flow Meter", believed to be published prior to Nov. 17, 1993.
Advertisement for "Astech Peak Flow Meter", believed to be published prior to Nov. 17, 1993.
Photographs of "Pocketpeak" peak flow meter manufactured by Ferraris Medical Ltd. Believed to be known or used prior to Nov. 17, 1993.
Photographs of "SPIR–O–FLOW" peak flow meter manufactured by Spirometrics, Inc. Believed to be known or used prior to Nov. 17, 1993.

(List continued on next page.)

*Primary Examiner*—Hezron E. Williams
*Assistant Examiner*—Harshad Patel
*Attorney, Agent, or Firm*—Brinks Hofer Gilson & Lione

[57] ABSTRACT

A peak flow meter is provided comprising an elongated body having a longitudinal direction and a predetermined cross sectional shape and a growing area. The body has an open entering end and an open exit end. The body is circumferentially continuous substantially from end to end. A piston and an indicator are mounted in said body for movement longitudinally thereof upon exhalation into the open entering end. The indicator is pushed along said body for movement by the piston longitudinally of said body. The indicator is of low mass so as not to overshoot, and is returned to rest by shaking a weight against it. A logarithmic scale is provided along said body against which the position of said indicator can be read.

42 Claims, 3 Drawing Sheets

OTHER PUBLICATIONS

EPO Search Report for EP 96 30 3201 dated Jul. 25, 1996.

Published EPO search report dated Mar. 3, 1995.

Copy of pamphlet entitled "Peak Flow Monitoring for Patients With Asthma", published by HealthScan Inc., dated 1990.

Manual entitled "Peak Performance A Strategy for Asthma Self–Assessment", by Guillermo R. Mendoza, M.D., dated 1987.

Copy of instruction manual for "ASSESS" peak flow meter manufactured by Healthscan Products, Inc., dated Aug. 1991.

Copy of instruction manual for "Personal Best" peak flow meter manufactured by Healthscan Products, Inc. dated 1994.

PEAK FLOW METER

This application is a continuation of application Ser. No. 08/153,091, filed Nov. 17, 1993 now abandoned.

BACKGROUND OF THE INVENTION

Many patients have respiratory problems, and it often is advantageous for a doctor to be able to ascertain the maximum peak rate of flow of a single forced expiration. It is further desirable to have a small instrument readily used by the patient himself to measure the peak flow. With a peak flow meter it is possible for the patient to ascertain if his peak flow rate remains at a more or less constant level, or if it deteriorates over time, or if it improves.

Instruments for such use, especially by patients, have been developed and are available commercially. However, the instruments now on the market are not fully satisfactory. They often have a member extending through a slot in a cylindrical body and blown along the body by a patient's exhalation into the cylindrical body. Such type of construction allows for entry of contaminants into the body, some of which leave residue that impairs movement of the indicator member along the slot. Most such meters have compressed scales which are difficult to read.

It is desirable that upon initial testing by the doctor a marker be applied to the meter indicating desirable range for the particular patient, as well as an improved range and a poor or deteriorating range. Such markers as known today are generally not satisfactory in that they are not capable of representing a percentage above or below the desirable range, since the desirable range for a given patient might be quite different from that of another patient. All that can be indicated is a fixed number above or below the desirable range, but there will be a different percentage of the desirable range depending upon where the desirable range is located on the meter.

In accordance with known meters, as indicated above, having a slot in the body through which the indicator moves, an opportunity is presented for a patient accidentally to block movement of the indicator with a misplaced finger. In the usual case the indicator is moved by a piston within the body, and as the piston travels along the body a progressively greater amount of air is expelled through the slot as the piston moves from rest position. Accordingly, the piston travels to a point at which the venting of air from the body balances a spring restraining the piston. Upon the cessation of blowing, the piston is returned to rest position by the spring, with the indicator remaining in the position reached until manually returned to rest position. The indicator must be of a relatively lightweight construction. If it is heavy, it will have inertia, and even though the piston stops, the indicator will continue to move according to its inertia, and thus introduce false readings. However, if the indicator is of extremely light weight and is exposed exteriorly of the body through the slot in which it moves, then it must be relatively fragile and susceptible to damage.

OBJECTS AND SUMMARY OF THE PRESENT INVENTION

It is an object of the present invention to provide an improved peak flow meter which is inexpensive to produce, long lived, and overcome the deficiencies of the prior art.

More particularly, it is an object of the present invention to provide a peak flow meter in which the moving indicator is disposed entirely within the confines of the elongated body, and wherein there is no longitudinal slot in the body as in the prior art.

Yet another object of the present invention is to provide a peak flow meter operating on a logarithmic scale, and which has a body expanding non-linearly to match such scale whereby progressively to bypass greater amounts of exhaled air as the piston moves away from rest position.

A further object of the present invention is to provide a peak flow meter in which an indicator or marker is moved along by a piston, wherein the indicator is of extremely low mass, and does not overshoot. It includes the provision o a weight or mass which is not attached to the indicator, but is used for returning the indicator to rest position.

In obtaining the foregoing and other objects I provide a peak flow meter having an elongated tube which expands in diameter from rest position to permit reading against a logarithmic scale. An axial tube is provided within the housing, and has a longitudinal slit therein. An indicator is retained on the tubing by means of an enlargement within the tubing, with a thinner portion extending through the slit. A piston of fixed diameter is spring urged toward the inlet end of the housing, and moves along the tube upon exhalation by a user. The indicator thus is moved along by the piston. However, the indicator is pushed by, but is not connected to the piston, and has a Spring therein bearing against the tube to hold the indicator in the position reached under the impetus of the piston. A weight or mass is contained within the tube, and moves ahead of the indicator. The indicator itself is of very low mass so that it does not overshoot. The weight is used to return the indicator to rest position for a subsequent use of the meter.

Since the indicator moves on a slot or slit in the central tube there is no need for a slot in the housing, whereby the housing is sealed except at the entering and exit ends. In keeping with the non-linear expansion of the housing the peak flow meter is provided with a longitudinal logarithmic scale against which the indicator is read.

THE DRAWINGS

The present invention best will be understood with reference the following specification when taken in connection with the accompanying drawings, wherein.

DETAILED DISCLOSURE OF THE ILLUSTRATED EMBODIMENT

Figure 1:
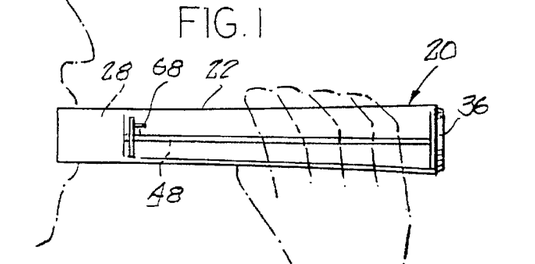
FIG. 1 is a side view of the peak flow meter of the present invention as used by patient.
Figure 2:
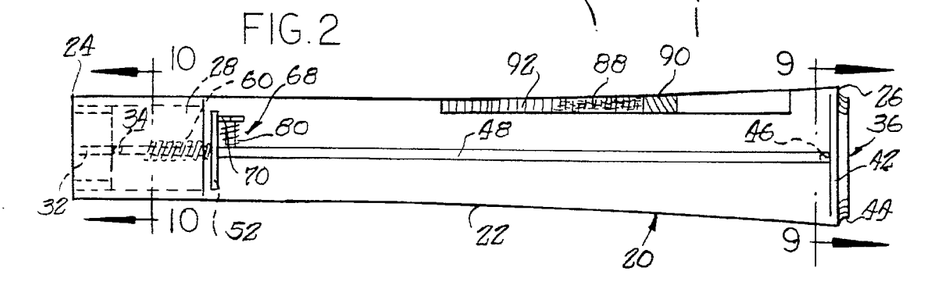
FIG. 2 is a more detailed view similar to FIG. 1 on an enlarged scale.
Figure 3:
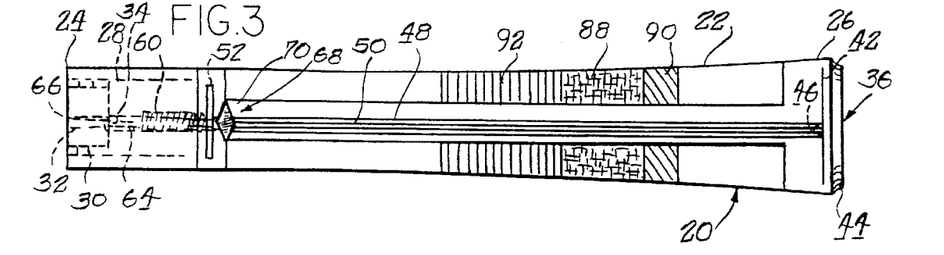
FIG. 3 is a top view of the peak flow meter as shown in FIG. 2.

Turning now in greater particularity to the drawings, and first to FIGS. 1–3, a peak flow meter 20 constructed in accordance with the principles of the present invention comprises an elongated body 22 of hollow, tubular construction. The body is smallest at its left or entering end 24, and expands to a maximum diameter at its right or exit end 26. The diameter and cross-sectional area do not expand on a linear basis, but rather to match a logarithmic scale. Hence, a longitudinal element of the body is not a straight line, but is concave outwardly. Looking at this from a mathematical standpoint, it is the generatrix that is outwardly curved. The body 22 is circumferencially completely closed, but is open at both ends. The body 22 preferably is made of plastic material which is transparent at least above the indicator shortly to be disclosed.

Figure 4:
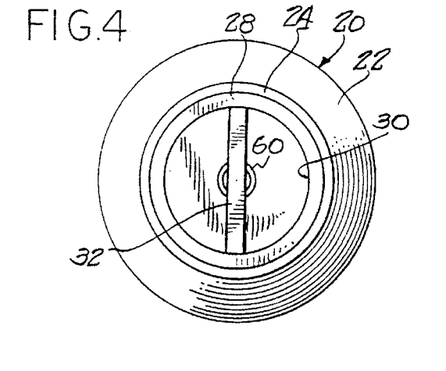
FIG. 4 is a left end view of the flow meter of FIGS. 2 and 3.

A plastic cylinder 28 is inserted in the left or entering end of the body. The cylinder 28 preferably is secured within the end of the body 22, such as by sonic or chemical welding. The major portion of the cylinder is of increasing inside diameter, but has a short portion at the extreme left end of reduced inside diameter. as indicated at 30 (see also FIGS. 4 and 10), A diametrical bar 32 extends across the portion of reduced diameter at 30, and the length of this portion. The bar is provided with a central longitudinally extending projection or pip 34, the purpose of which will be apparent shortly.

Figure 5:
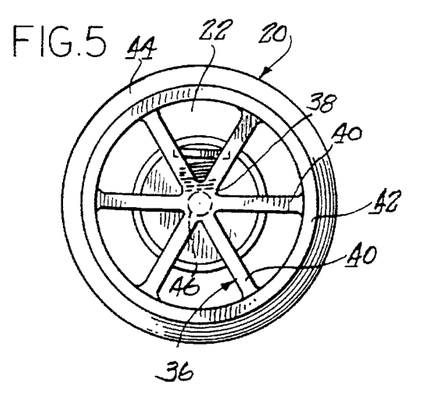
FIG. 5 is a right end view of the flow meter.

As will be seen in FIG. 2, the left or entering end of the body 22 comprises a mouthpiece, and is designed to be placed within a patient's mouth for exhalation. Considering the direction of air flow through the peak flow meter 20, the left end may also be considered as the upstream end, whereas the right or exit end may be considered as the downstream end. In any event, the right end is provided with a spider 36 (see FIGS. 5 and 9) having a central hub 38 and a plurality of radial arms or spokes 40 extending to a circular rim 42 having an outer diameter fitting snugly within the inner diameter of the right end of the body 22. Outwardly of the rim there is an integral cap 44 of greater diameter at its maximum equaling the outer diameter of the end 26, and preferably tapering inwardly therefrom. The spider 36 fits snugly and frictionally within the right end 26 of the body. In this embodiment of the invention it is not permanently secured to the body. Similarly, the cylinder 28 at the left or entering end could be held in place simply by a friction fit rather than being permanently secured in place. The central hub 38 is provided with an axial projection or pip 46 which is aligned with the pip 34.

All of the parts herefore referred to are constructed of a resinous plastic material (commonly referred to as plastic) which is molded to the desired shape by known molding methods. Axially of the body there is a metallic tube 48 extending nearly the entire length of the body and having its opposite ends centered on and supported by the pips 34 and 46. The inside diameter of the tube is related to the outside diameter of the pips so as to form a snug fit. A narrow straight slit 50 extends longitudinally of the tube 48 from end to end thereof. Attention should be paid to FIGS. 6–8 along with FIGS. 1–3 at this point. A piston 52 is slidable on the tube 48 longitudinally of the tube. The piston comprises a transverse disk 54 of fixed outside diameter less than the internal diameter of the body 22 of the peak flow meter 20. An integral cylinder 56 extends axially from the disk 54 in the direction of the entering end 24 of the body. The disk 54 and cylinder 56 have a common bore of very slightly greater diameter than the outside diameter of the tube 48 to allow sliding thereon. The disk and cylinder are preferably molded of a suitable plastic.

The cylinder 56 immediately adjacent the disk 54 is provided with a reduced diameter circumferential notch 58. A helical spring 60 tensionally urges the piston back toward the entering end 24. The inside diameter of the spring 60 is substantially greater than the outside diameter of the tube 48 so as to fit loosely there-about, and is of substantially the same diameter as the outside diameter of the cylinder 56. However, the last two turns of the spring 60, as indicated at 62 are of reduced diameter so as to grip within the notch 58, and thereby attach the spring to the piston. The opposite end of the spring is provided with an elongated portion 64 having a re-entrant end 66 which loops over the end of the tube and is firmly held in place thereon by an interference fit with the pip 34.

Also slidable along the tube 48, and specifically in the slit or slot 50 therein, is a marker 68. The marker has a generally T-shaped cross section having at the top thereof a diamond shaped indicator 70, with the major axis of the diamond arranged transversely of the slit 50. The marker also includes a stem 72 depending from the indicator 70. The upper portion of the stem is semi-cylindrical 74, while a lower portion comprises a flat plate 76 slidably fitting within the tube slot 50. At the bottom of the stem is an enlargement 78 somewhat less than a semi-cylinder and fitting inside the tube. A coil spring 80 encircles the stem 72 and is fairly lightly compressed between the tube 48 and the underside of the indicator 70. The spring 80 holds the marker frictionally at whatever point it happens to be along the tube 48.

The marker is of very low mass, and moves along ahead of the disk 54 of the piston 52 as the latter advances against the tension of the spring 60 as the entering end of the peak flow meter is blown into as indicated in FIG. 1. When the piston reaches a balance point between blowing force and the spring, it stops. The marker 68 also stops at the same time as the piston due to its low mass, and does not overshoot as has often been a problem in the prior art.

The piston 52 retracts to rest position as determined by the turns of the coil spring 60 engaging one another when a patient stops blowing. The marker stays at the position reached until returned for another exhalation test. The marker, being of very low mass, is not satisfactorily returned to its rest position gravitationally, or by shaking. In order to return the marker, I provide a cylindrical slug 82 of a appreciable mass downstream of the marker. This mass is of no great significance as the piston and marker advance, and when the piston stops any inertia build up in the slug simply causes it to move further along the tube with no influence on the position of the marker. However, the flow meter may be held in the hand, and shaken down, much in the manner of shaking down a fever thermometer. The mass presses or pounds against the marker and returns it to rest position against the piston as shown in FIGS. 1–3.

Figures 6, 7, 7A, 8, 9, 10, 11:
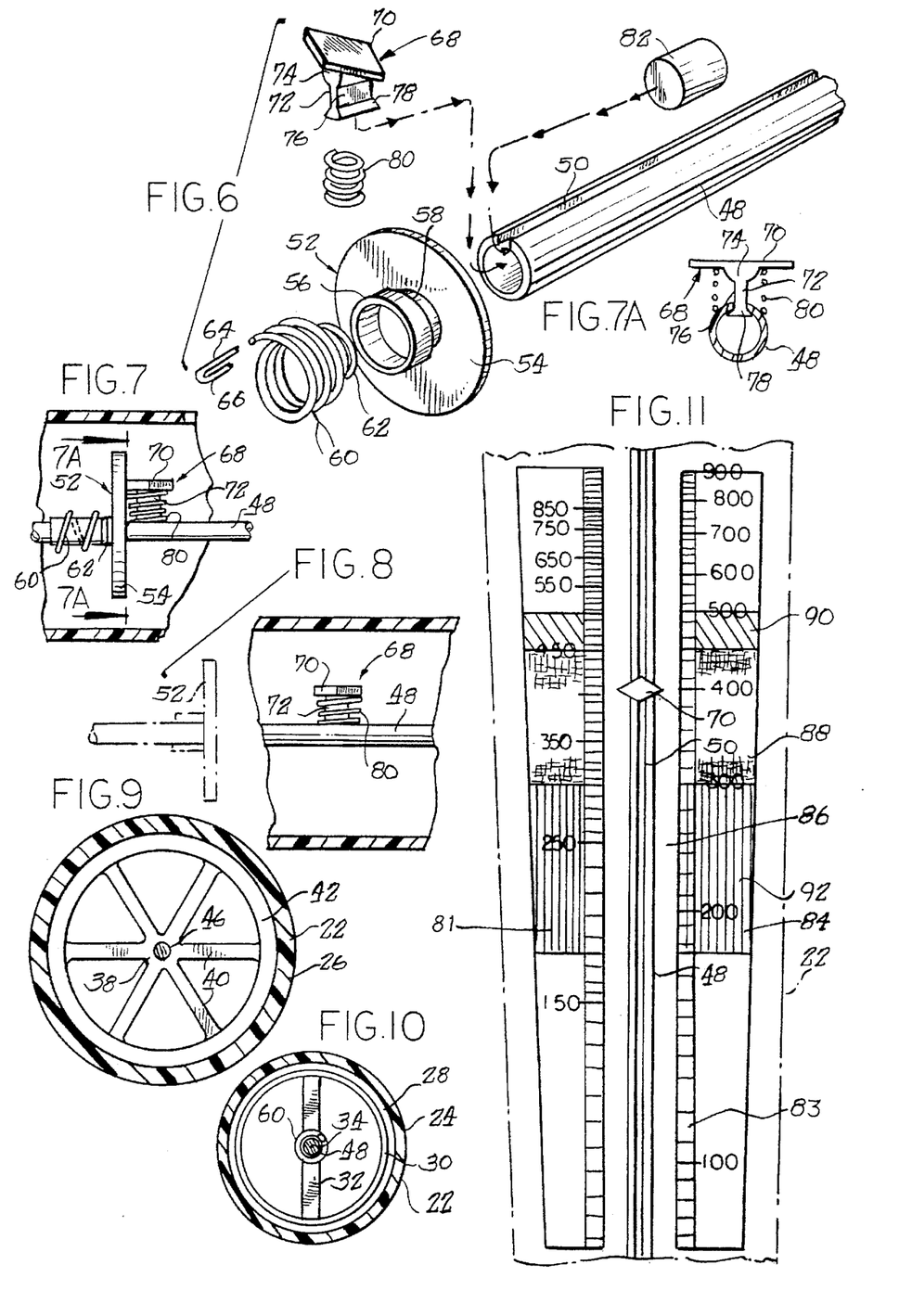
FIG. 6 is a fragmentary exploded perspective view of the central slitted tube of the flow meter and the parts associated therewith.
FIG. 7 is a fragmentary longitudinal sectional view of a portion of the flow meter.
FIG. 7A is a partial cross-sectional view as taken substantially along the line 7A—7A in FIG. 7.
FIG. 8 is a fragmentary longitudinal sectional view similar to FIG. 7 showing the parts in a different position of operation.
FIG. 9 is an enlarged cross-sectional view taken substantially along the line 9—9 in FIG. 2.
FIG. 10 is a cross-sectional view as taken substantially along the line 10—10 in FIG. 2.
FIG. 11 is a fragmentary top view of the present peak flow meter on a substantially enlarged scale showing the logarithmic longitudinal scale of the flow meter.
Figure 12:
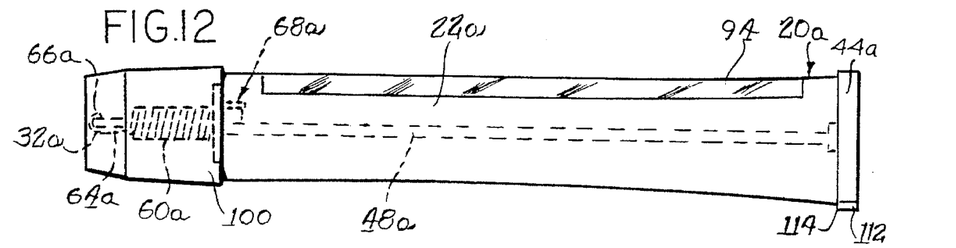
FIG. 12 is a side view generally similar to FIG. 2 of an improved form of the invention.
Figure 13:
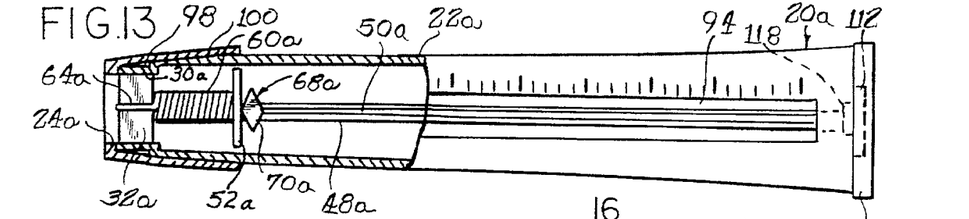
FIG. 13 is a top view generally similar to FIG. 3 and corresponding to the improved form of the invention in FIG. 12.

The logarithmic scale 83 referred to is shown rather generally in FIGS. 2 and 3, and specifically in FIG. 11. The markings and numerals, best seen in FIG. 11, are on a logarithmic scale. It readily will be appreciated that the scale is progressively compressed as one moves upscale, as are the associated numbers. The scale preferably is molded in or printed directly on the plastic material of the body 22. In addition to this, a transparent tape is supplied with the meter, and is adhesively secured to the surface of the body 22 above and aligned with the slot 50 in the tube 48. As a practical matter, there may be two parallel strips of adhesive tape 81 and 84 leaving a clear channel 86 between them. Alternatively, the two strips can be made as one, with a clear section in the middle to permit viewing of the tube and of the slider indicator 70. The tape or tapes are provided with a longitudinally central area 88 of a chosen color, light yellow being exemplary. A downstream band 90 therefrom preferably is green, and an upstream band 92 is red. It will be observed that the bands are progressively narrower from input to output end of the meter. The doctor by test determines what is a reasonable range for a given patient's peak exhalation, and the green portion 90 is applied in that area. If the patient is always successful at home in producing movement of the indicator 70 into that area, then there is no need for the patient to see his doctor immediately. However, if the indicator falls in the red zone 92, he should call his doctor immediately. If the indicator stops in the yellow area he should be wary. If he can re-enter the green area all is well, but if he falls into the red area he should contact his doctor promptly.

A logarithmic scale is excellent for reading, since it is expanded in the low area where a patient's exhalation is critical. As the exhalation moves upscale, the markings are compressed, but this is of less importance since the patient is doing well if he can get into this higher area. Due to the logarithmic nature of the scale the bands comprise fixed percentages, no matter where the tape or tapes are placed along the scale.

The cross sectional area of the body is not itself directly on a logarithmic scale, but is empirically related to the logarithmic reading scale so that proper readings are obtained. Empirical results provide the final determination of diameter and cross sectional area.

It will now be apparent that the parts of the meter are housed entirely within the body of the meter. A stray finger cannot stop the indicator, and the indicator cannot be manually advanced beyond its stopping place from a breath exhalation. As has been noted heretofore, the marker is of very low mass, and does not overshoot the position to which it is moved by the piston. The low mass of the marker makes it impossible to return it directly by a shaking or stamping motion, but the metallic pellet within the tube relatively easily returns the marker to rest position.

It will be appreciated that some contaminants do enter the body of the meter along with the patient's breath. This can result in reading inaccuracies, but the period of time before any inaccuracy might appear is much greater than in prior art peak flow meters in which the marker or indicator rides in a slot and partially extends from the body of the meter. From time to time the meter may be flushed out by running water or other mild cleaning fluid through the peak flow meter from end to end.

Various improvements have been made in the present peak flow meter in readying the device for production and sale. Such improvements are illustrated in FIGS. 12–19. Most of the parts are the same or similar to those previously described, and similar numerals are utilized with the addition of the suffix a to identify similar parts. Thus, the peak flow meter 20a comprises a body of hollow, tubular construction which enlarges non-linearly from the left or entering end to the right or exit end. Most of the body is frosted on the interior surface thereof as a part of the manufacturing process. This presents a more attractive appearance than a totally clear body, and concentrates vision on the important internal parts, and minimizes distractions that might be caused by internal condensation. A rectangular, elongated portion 94 aligned with the tube 48a remains clear, and the indicator 70a is visible through this area. Another area 96 180° from the clear area 94 also is clear for display of the manufacturer's trademark, etc.

The entering end 24a of the body 22a is of unitary construction, and the current portion of the body immediately adjacent to the entering end comprises an inwardly stepped cylinder 98 molded as an integral portion of the remainder of the body 22a. The diametrical bar 32a is also integral with the inwardly stepped cylinder 98 and the remainder of the body 22a. A mouthpiece 100 fits over the entering end and is removable therefrom and is removable for cleaning.

Figures 14, 15, 16, 17, 18, 19:
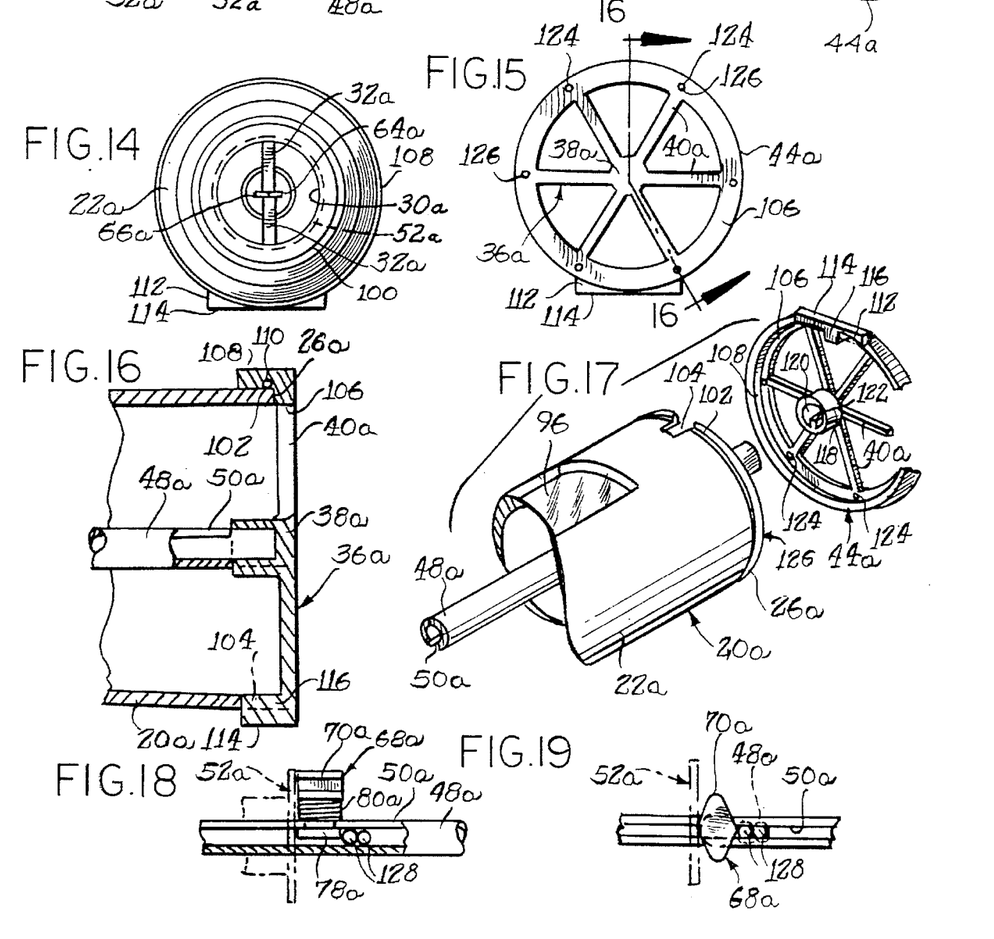
FIG. 14 is a left end view of the invention as shown in FIG. 12.
FIG. 15 is a right end view of the form of the invention shown in FIG. 12.
FIG. 16 is a sectional view as taken along the line 16—16 in FIG. 15.
FIG. 17 is an exploded perspective view of the right or exit end of the invention as shown in FIGS. 12-15, but inverted in order best to show certain features of the invention.
FIG. 18 is a fragmentary side view partially in section showing details of the marker and returning mass.
FIG. 19 is a fragmentary top view corresponding to FIG. 18.

The right end 26a of the body 22a is best seen in FIGS. 16 and 17. It is shown in upright position in FIG. 16, but the entire assembly has been inverted or rotated 180° in FIG. 17 in order to show certain parts to best advantage. The end 26a is provided with a peripheral ridge 102, and with a rectangular notch 104 leading into the end of the body. An end cap 44a is provided with a flange 106 which abuts the right end 26a of the body. An annular flange 108 extends to the left from the flange 106 and grips the outer wall of the body 22a. The interior annular recess 110 in this annular flange 108 receives the annular ridge 102 at the end 26a of the body 22a, and partially serves to retain the cap 44a on the end of the body.

The cap 44a further is provided with a projection or enlargement 112 which provides a flat, tangent surface 114 which prevents rolling of the peak flow meter when placed on a table or other horizontal supporting surface. A radially inwardly projecting member or tang 116 extends from the enlargement 112 and annular flange 108 and is received in the notch or recess 104 at the end of the body to ensure proper rotational alignment of the body and of the end cap 44a.

A cup 118 extends axially of the body inwardly from the hub 38a of the end cap 44a, being provided with a central well or opening 120. A key 122 extends radially in from the sidewall of the cup, and is received in the slot 50a of the tube 48a to ensure proper rotational alignment of the tube 48a with the end cap 44a. It will be observed that the key 122 is displaced 180°, whereby the open portion of the tube, and the indicator 70a will be properly aligned with the clear viewing area 94 of the body, and will be upwardly directed if the peak flow meter is placed on a table or the like due to the positioning by the tangent surface 114.

The end wall or flange 106 of the end cap 44a is provided with six through-holes 124 respectively aligned with the arms or spokes 40a of the spider 36a. Axial projections or studs 126 are spaced about the end 26a of the body and project through the holes 124. The studs are permanently secured in the holes by a sonic welding process.

The cylindrical mass 82 initially used for return of the marker 68 sometimes does not move as freely within the tube 48 as is desired. This is particularly true with aging of the peak flow meter and accumulation of oxides, dirt, etc. Such possible sticking has been overcome by providing two spherical balls 128 downstream of the base 78a of the marker 68a. Considerably less mass is provided by the two balls 128 as contrasted with the cylinder 82, thus minimizing any resistance to movement of the marker when blown downstream by a patient and the piston 52a. The contacting surfaces of the balls with the inner surface of the slotted tube are much less in area than the contacting surfaces of the previous cylindrical mass with the inner wall of the tube. Thus, there is substantially no sticking or binding of the balls 128 within the tube, and the marker is readily returned to rest position by shaking of the peak flow meter in the manner of a fever thermometer, notwithstanding the lesser mass of the balls.

Initially the low mass of the marker 68 precluded overshoot thereof when tested on a standard square wave flow machine. However, I discovered experimentally that some people with normal lung capacity could initially exert a spike of high pressure that caused the marker to overshoot. This is believed to be true of many or perhaps all commercial peak flow meters now known, but I considered any overshoot to be unacceptable.

I discovered experimentally that the length of the entering end portion 24a is of little consequence, but that the diameter (and hence area) is important in limiting the initial spike of increased air pressure entering the peak flow meter. I have further found that with the inside diameter of the entering end portion limited to not more than about 0.545 inch the mariner cannot be made to overshoot either by a test machine or by a normally healthy person with strong exhalation. The length of the entering end portion 24a is 0.400 inch.

It has been mentioned earlier, but is worthy of repetition that no matter where the tape is placed by the doctor axially of the flow meter the three colored bans 88,90, and 92 respectively comprise a fixed percentage off logarithmic scale. Three colored bands have been illustrated, but greater or lesser numbers could be used, and the bands could be discerned other than by color.

The specific embodiments of the invention as herein shown and described are for illustrative purposes. Various changes in structure will no doubt occur to those skilled in the art, and will be understood as forming a part of the present invention insofar as they fall within the spirit and scope of the appended claims.

The invention is claimed as follows:

1. A peak flow meter comprising an elongated body having a longitudinal direction and a predetermined cross sectional shape, said body having an open entering end and an open exit end, a piston and an indicator, means for mounting said piston in said body for longitudinal movement thereof upon exhalation into said open entering end, means for mounting said indicator in said body for engagement by said piston for movement by said piston longitudinally of said body, said indicator staying in the position to which it has been moved by said piston, means for retracting said piston independently of said indicator, a mass longitudinally movable in said body for returning said indicator independently of said piston, and means along said body against which the position of said indicator can be read.

2. A peak flow meter as set forth in claim 1 and further including a spring operatively connected to said piston for limiting advance of said piston and for retracting said piston.

3. A peak flow meter as set forth in claim 2 wherein said spring comprises a tension spring.

4. A peak flow meter as set forth in claim 1 wherein said piston mounting means and said indicator means comprise an elongated member extending substantially longitudinally of said body and along which said piston and said indicator are movable.

5. A peak flow meter as set forth in claim 4 wherein said elongated member is cylindrical, and wherein said elongated cylindrical member comprises a hollow tube having a longitudinal slot therein substantially from end to end and a means for carrying said indicator slidably mounted in said slot.

6. A peak flow meter as set forth in claim 5 wherein said indicator and carrying means therefore are substantially T-shaped having a stem extending through said slot, an enlargement on said stem interiorally of said tube, and a spring compressed between said indicator and said tube.

7. A peak flow meter as set forth in claim 5 wherein said indicator and said carrying means for said indicator have low mass, and a mass longitudinally movable in said body for returning said carrying means and said indicator toward the entering end of said body.

8. A peak flow meter as set forth in claim 7 wherein said mass is slidably mounted within said tube.

9. A peak flow meter as set forth in claim 8 wherein the mass comprises a cylinder.

10. A peak flow meter as set forth in claim 8 wherein the mass comprises spherical means.

11. A peak flow meter as set forth in claim 1 wherein said piston has a predetermined fixed cross sectional area, and wherein said body has an increasing internal area from said entering end toward said exit end and of greater area than said predetermined area of said piston.

12. A peak flow meter as set forth in claim 11 wherein both said body and said piston have a circular cross section.

13. A peak flow meter as set forth in claim 11 and further including a logarithmic scale on said body for reading the position of said indicator.

14. A peak flow meter as set forth in claim 13 wherein both said body and said piston have a circular cross section.

15. A peak flow meter comprising an elongated body having a longitudinal direction and a predetermined cross sectional shape, said body having an open entering end and an open exit end, a piston with a predetermined cross sectional area, means for mounting said piston in said body for longitudinal movement thereof upon exhalation into said open entering end, an indicator mounted internally of said body and independently of said piston for movement by said piston longitudinally of said body, said piston having a fixed predetermined cross sectional area, said body having a cross sectional area varying logarithmic along said longitudinal direction, and means along said body against which the position of said indicator can be read.

16. A peak flow meter as set forth in claim 15 wherein said body cross sectional area is greater at the exit end than at the entering end.

17. The peak flow meter as set forth in claim 16 wherein said means along said body for reading the position of said indicator comprises a logarithmic scale.

18. A peak flow meter for determining peak air flow of an exhaling patient, comprising:

a hollow body for accommodating a flow of exhaled air therethrough;

an indicator adjacent to said body and movable relative to said body to a position along a scale on said body, said position related to a peak of the flow of exhaled air through said body;

said body having an internal area related to said scale such that said scale represents a logarithmic scale of the peak of the exhaled flow of air through said body; and at least one zone adjacent said logarithmic scale said zone indicating a predetermined range of a patient's air flow independent of placement along said logarithmic scale.

19. The peak flow meter of claim 18 said flow meter further comprising:

a mouthpiece connected to said body and into which the patient blows air.

20. The peak flow meter of claim 18 wherein said at least one zone is positioned on an approval tape affixable adjacent said scale.

21. The peak flow meter of claim 20 wherein said approval tape includes a plurality of zones.

22. The peak flow meter of claim 21 wherein the zones on the tape are related logarithmically to the scale.

23. The peak flow meter of claim 20 wherein said approval tape is affixable to said scale at various locations.

24. The peak flow meter of claim 20 wherein said approval tape includes a plurality of zones representing fixed percentage ranges.

25. The peak flow meter of claim 20 wherein said approval tape includes a green zone representing a clinically determined reasonable range for the patient's peak air flow.

26. The peak flow meter of claim 20 wherein said approval tape includes a yellow zone representing a range indicating that a patient should be wary of the potential need of medical attention.

27. The peak flow meter of claim 20 wherein said approval tape includes a red zone representing a range indicating a need for obtaining medical attention.

28. The peak flow meter of claim 18, said flow meter further comprising:

a plurality of approval tapes to be positioned on said body adjacent said scale.

29. The peak flow meter of claim 18 wherein said scale includes markings.

30. The peak flow meter of claim 29 wherein said markings represent the peak air flow through the body.

31. A peak flow meter comprising:

a hollow elongated body;

an entering end on the hollow elongated body for receiving a flow of air;

an exit end opposite the entering end;

an indicator adjacent to said body and movable relative to said body to a position along a scale on said body, said position related to a peak of the flow of air through said body;

said scale being a logarithmic scale extending longitudinally along the body; and said hollow elongated body having a non-linearly expanding diameter designed to cooperate with the logarithmic scale.

32. The peak flow meter of claim 31 wherein the diameter of the hollow elongated body enlarges non-linearly from the entering end to a maximum diameter at the exit end.

33. The peak flow meter of claim 31 wherein the logarithmic scale is expanded in an area representing lower exhalation.

34. The peak flow meter of claim 31 wherein the logarithmic scale is compressed in an area representing higher exhalation.

35. The peak flow meter of claim 31 wherein the peak flow meter further comprises:

a transparent tape having a plurality of contiguous bands for marking a reasonable range of exhalation.

36. The peak flow meter of claim 35 wherein the plurality of bands are different colors.

37. The peak flow meter of claim 35 wherein the tape is adhesively securable to the peak flow meter.

38. The peak flow meter of claim 35 wherein the tape has a clear longitudinal section and two parallel sections of colored bands extending longitudinally on either side of the clear longitudinal section.

39. A peak flow meter comprising:

a hollow elongated body;

an entering end on the hollow elongated body for receiving a flow of air;

an exit end opposite the entering end;

a longitudinal tube inside the hollow elongated body extending substantially from the entering end to the exit end;

a piston slidably mounted on the longitudinal tube;

an indicator slidably mounted on the longitudinal tube, said indicator separate from the piston and positioned between the piston and the exit end;

an indicator return mass for returning the indicator to a rest position separately from the piston;

a logarithmic scale on the hollow elongated body, said logarithmic scale extending longitudinally along the body; and said hollow elongated body having a non-linearly expanding diameter designed to cooperate with the logarithmic scale.

40. The peak flow meter of claim 39 wherein the hollow elongated body has an interior surface, said interior surface having a frosted portion and a clear portion.

41. The peak flow meter of claim 40 wherein the clear portion is a rectangular portion extending longitudinally along the body whereby the clear portion is aligned so that the indicator is viewed through the clear portion.

42. The peak flow meter of claim 39 wherein the hollow elongated body is tubular and completely closed circumferentially.

* * * * *

UNITED STATES PATENT AND TRADEMARK OFFICE
CERTIFICATE OF CORRECTION

PATENT NO. : 5,627,324
DATED : May 6, 1997
INVENTOR(S) : William R. Shene

It is certified that error appears in the above-indentified patent and that said Letters Patent is hereby corrected as shown below:

<u>On the Title Page</u>

In column 2, item [56], line 4, under "FOREIGN PATENT DOCUMENTS", change "WIPO" to --EPO--.

<u>In the Claims</u>

In claim 18, line 12, after "scale" insert --,-- (comma).

Signed and Sealed this

Twentieth Day of June, 2000

Attest:

Q. TODD DICKINSON

*Attesting Officer*  *Director of Patents and Trademarks*